United States Patent
Chang

(10) Patent No.: US 9,528,964 B2
(45) Date of Patent: Dec. 27, 2016

(54) METHOD OF DETECTING A STATE OF A COATED GEL

(71) Applicants: QISDA (SUZHOU) CO., Ltd., Suzhou, Jiangsu Province (CN); QISDA CORPORATION, Taoyuan County (TW)

(72) Inventor: Tang-Chen Chang, Hsinchu County (TW)

(73) Assignee: Qisda Corporation, Taoyuan County (TW)

(*) Notice: Subject to any disclaimer, the term of this patent is extended or adjusted under 35 U.S.C. 154(b) by 339 days.

(21) Appl. No.: 14/249,347

(22) Filed: Apr. 9, 2014

(65) Prior Publication Data
US 2014/0305218 A1    Oct. 16, 2014

(30) Foreign Application Priority Data

Apr. 11, 2013 (TW) .............................. 102112885 A

(51) Int. Cl.
*G01N 29/11* (2006.01)
*G01N 29/48* (2006.01)
*G01N 29/06* (2006.01)

(52) U.S. Cl.
CPC ........... *G01N 29/0654* (2013.01); *G01N 29/11* (2013.01); *G01N 29/48* (2013.01)

(58) Field of Classification Search
CPC ..... G01N 29/0654; G01N 29/11; G01N 29/48
USPC .......................................................... 73/620
See application file for complete search history.

(56) References Cited

U.S. PATENT DOCUMENTS

| 2008/0139944 A1* | 6/2008 | Weymer | A61B 8/4281 |
| | | | 600/459 |
| 2012/0035480 A1 | 2/2012 | Migita | |
| 2014/0290369 A1* | 10/2014 | Kiyose | A61B 8/4494 |
| | | | 73/632 |

FOREIGN PATENT DOCUMENTS

| CN | 201522478 | * | 7/2010 |
| CN | 102245108 A | | 11/2011 |
| CN | 103278566 | * | 9/2013 |
| JP | 09133661 | * | 5/1997 |
| JP | 2001330662 | * | 11/2001 |
| KR | 101121550 | * | 3/2012 |

* cited by examiner

*Primary Examiner* — J M Saint Surin

(57) ABSTRACT

A method of detecting a state of a coated gel coated on an ultrasound probe includes coating a gel on the ultrasound probe, scanning and generating a scanned image, dividing the scanned image into a strong echo area and a weak echo area, and detecting signal variation in the strong echo area of the scanned image to determine the state of the coated gel coated on the ultrasound probe.

20 Claims, 4 Drawing Sheets

METHOD OF DETECTING A STATE OF A COATED GEL

BACKGROUND OF THE INVENTION

1. Field of the Invention

The present invention relates to a method of detecting a state of a coated gel coated on an ultrasound probe, and more specifically, to a method of detecting whether the coated gel measures up to a standard.

2. Description of the Prior Art

An ultrasound scanner is generally used in a nondestructive test, and the ultrasound scanner emits ultrasound signals and receives the echo ultrasound signal of the reflected by objects for detection. An ultrasound probe of the ultrasound scanner includes precise ultrasound elements for detecting signal intensity. However, the ultrasound elements will wear after being used for a long time, so that parameters of the ultrasound elements must be calibrated to meet the requirements of ultrasound detection. Besides, a gel is coated on the ultrasound probe as a media when scanning the object by the ultrasound probe, so as to reduce the energy loss of the ultrasound through the contact with air. However, as the gel thickness is insufficient or the connection between the gel and the ultrasound probe is inadequate, it results in lack of clarity and distortion of the scanned image.

SUMMARY OF THE INVENTION

The present invention is to provide a method of detecting a state of a coated gel coated on an ultrasound probe to enhance the performance of the ultrasound detection.

According to the disclosure, a method of detecting a state of the coated gel coated on an ultrasound probe includes coating a gel on the ultrasound probe, scanning and generating a scanned image, dividing the scanned image into a strong echo area and a weak echo area, and detecting signal variation in the strong echo area of the scanned image to determine the state of the coated gel coated on the ultrasound probe.

According to the disclosure, a method of supplying the gel on an ultrasound probe includes providing a gel supplying unit coupled to the ultrasound probe, scanning and generating a scanned image, dividing the scanned image into a strong echo area and a weak echo area, and detecting signal variation in the strong echo area of the scanned image to selectively supply the gel on the ultrasound probe by the gel supplying unit.

The method of the present invention includes detecting the state of the coated gel coated on the ultrasound probe for determining whether the thickness, the connection and the consistency of the coated gel coated on the ultrasound probe measure up. As the thickness, the connection and the consistency of the coated gel do not measure up, a corresponding information that the thickness, the connection and the consistency of the coated gel do not measure up can be displayed on the user interface, and the gel supplying unit can supply the gel on the ultrasound probe. Therefore, the performance of the ultrasound probe can be enhanced.

These and other objectives of the present invention will no doubt become obvious to those of ordinary skill in the art after reading the following detailed description of the preferred embodiment that is illustrated in the various figures and drawings.

DETAILED DESCRIPTION

Figure 1:
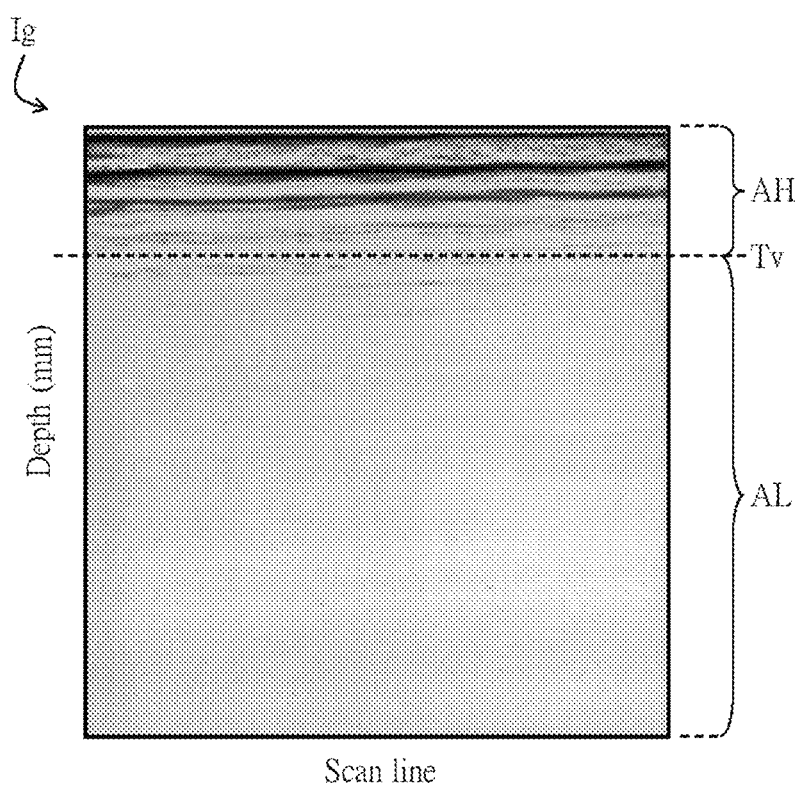
FIG. 1 is a diagram of a standard image generated by an ultrasound probe and displayed on a user interface according to an embodiment of the present invention.
Figure 2:
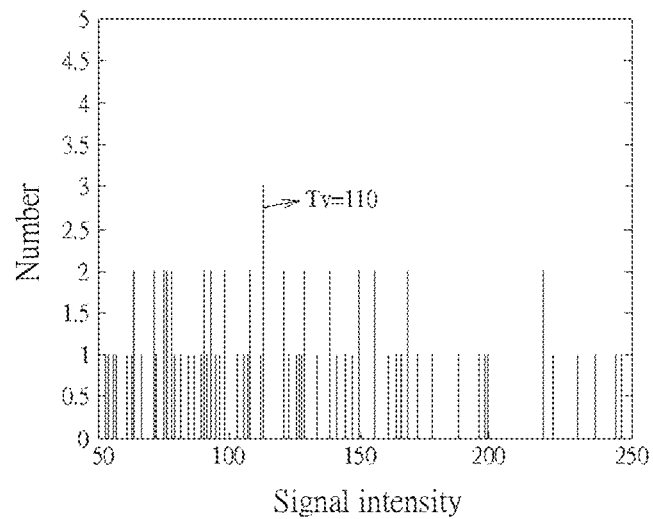
FIG. 2 is a diagram of a signal intensity distribution of scan lines of the standard image for generating a critical intensity value according to the embodiment of the present invention.
Figure 3:
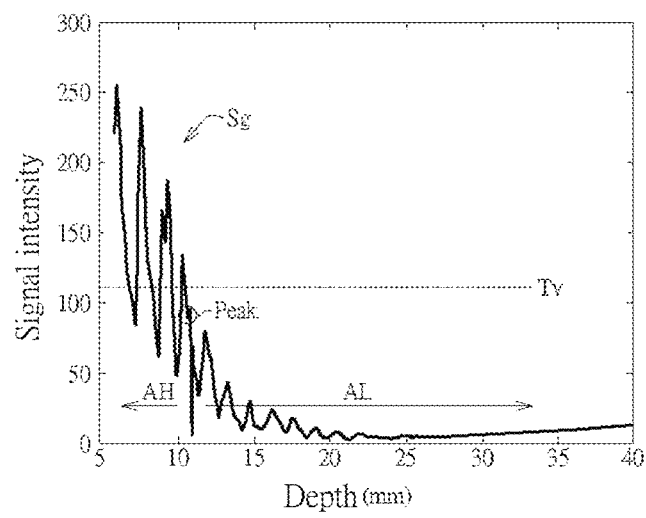
FIG. 3 is a diagram of dividing the standard image into a strong echo area and a weak echo area by the critical intensity value according to the embodiment of the present invention.

Please refer to FIG. 1 to FIG. 3. FIG. 1 is a diagram of a standard image Ig generated by an ultrasound probe and displayed on a user interface according to an embodiment of the present invention. FIG. 2 is a diagram of a signal intensity distribution of scan lines of the standard image Ig for generating a critical intensity value Tv according to the embodiment of the present invention. FIG. 3 is a diagram of dividing the standard image Ig into a strong echo area AH and a weak echo area AL by the critical intensity value Tv according to the embodiment of the present invention.

As shown in FIG. 1, after an ultrasound scanner is turned on to emit ultrasound, the ultrasound probe can receive an echo signal for generating the standard image Ig. According to the embodiment, the standard image Ig may not be regenerated every time the ultrasound scanner is turned on, and the standard image Ig may be generated once and saved as an image file for the following comparison of detection.

Please refer to FIG. 2, signal intensity values of the scan lines of the standard image Ig are averaged to calculate signal intensity average values corresponding to different depths according to the signal intensity distribution of the scan lines of the standard image Ig. And then, the signal intensity average values corresponding to the different depths can be statistically analyzed to generate the critical intensity value Tv for roughly dividing the standard image Ig into the strong echo area AH and the weak echo area AL.

According to one embodiment, the critical intensity value Tv can be determined as a signal intensity value with a greatest number of signals among all the signal intensity values. For example, as shown in FIG. 2, the signal intensity value with the greatest number of signals is 110, so that the critical intensity value Tv is set to 110. As shown in FIG. 3, after the critical intensity value Tv is calculated, a boundary between the strong echo area AH and the weak echo area AL of the standard image Ig can be determined to be a first peak value lower than the critical intensity value Tv, so that the standard image Ig can be divided into the strong echo area AH and the weak echo area AL.

Figure 4:
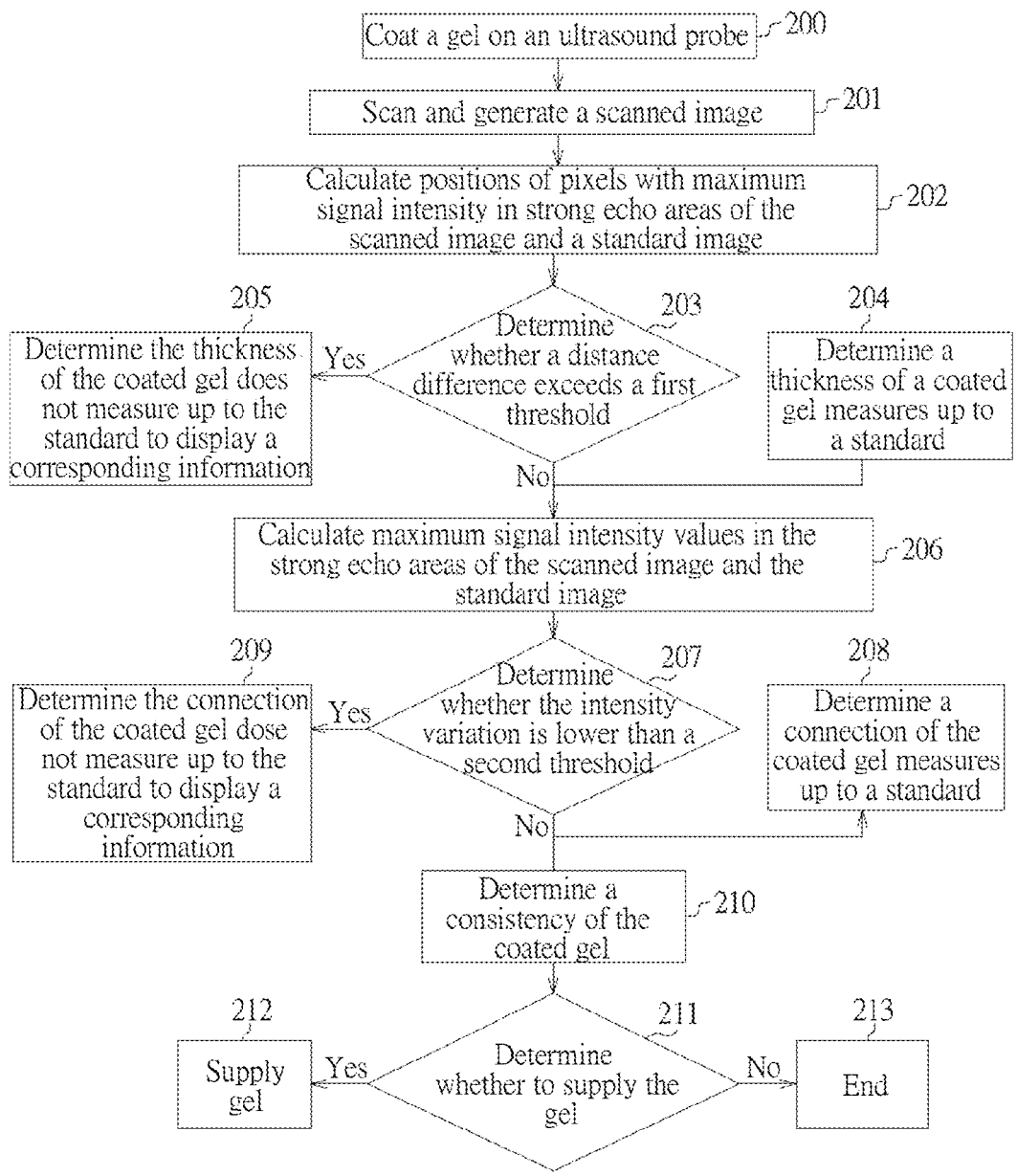
FIG. 4 is a flow chart of a method of detecting a state of a coated gel coated on the ultrasound probe according to the embodiment of the present invention.

Please refer to FIG. 4. FIG. 4 is a flow chart of a method of detecting a state of a coated gel coated on the ultrasound probe according to the embodiment of the present invention. The method includes the following steps:

Step 200: Provide a gel supplying unit coupled to the ultrasound probe and coat the gel on the ultrasound probe.

Step 201: Scan and generate a scanned image Sg by the ultrasound probe with the coated gel and divide the scanned image Sg into a strong echo area AH and a weak echo area AL.

Step 202: Compare signal intensity in the strong echo area AH of the scanned image Sg with signal intensity in the strong echo area AH of the standard image Ig, so as to calculate positions of pixels with maximum signal intensity corresponding to the scan lines in the strong echo areas AH of the scanned image Sg and the standard image Ig.

Step 203: Calculate a distance difference between the positions of the pixels with the maximum signal intensity of the scanned image Sg and the standard image Ig, and then determine whether the distance difference between the positions of the pixels with the maximum signal intensity of the scanned image Sg and the standard image Ig exceeds a first threshold. If yes, got to step 205; if no, go to steps 204 and 206.

Step 204: Determine a thickness of the coated gel measures up to a standard as the distance difference between the positions of the pixels with the maximum signal intensity of the scanned image Sg and the standard image Ig is less than the first threshold.

Step 205: Determine the thickness of the coated gel does not measure up to standard to display a corresponding information that the thickness of the coated gel does not measure up to the standard on the user interface as the distance difference between the positions of the pixels with the maximum signal intensity of the scanned image Sg and the standard image Ig exceeds the first threshold.

Step 206: Compare signal intensity in the strong echo area AH of the scanned image Sg with signal intensity in the strong echo area AH of the standard image Ig, so as to calculate maximum signal intensity values corresponding to the scan lines in the strong echo areas AH of the scanned image Sg and the standard image Ig.

Step 207: Calculate an intensity variation between the maximum signal intensity values corresponding to the scan lines in the strong echo areas AH of the scanned image Sg and the standard image Ig, and then determine whether the intensity variation between the maximum signal intensity values corresponding to the scan lines in the strong echo areas AH of the scanned image Sg and the standard image Ig is lower than a second threshold. If yes, got to step 209; if no, go to steps 208 and 210.

Step 208: Determine a connection of the coated gel measures up to a standard as the intensity variation between the maximum signal intensity values corresponding to the scan lines in the strong echo areas AH of the scanned image Sg and the standard image Ig exceeds the second threshold.

Step 209: Determine the connection of the coated gel dose not measures up to a standard to display a corresponding information that the connection of the coated gel does not measure up to the standard on the user interface, as the intensity variation between the maximum signal intensity values corresponding to the scan lines in the strong echo areas AH of the scanned image Sg and the standard image Ig is lower than the second threshold.

Step 210: Determine a consistency of the coated gel according to the distance difference between the positions of pixels with maximum signal intensity in the strong echo areas AH of the scanned image Sg and the standard image Ig, and the intensity variation between the maximum signal intensity values corresponding to the scan lines in the strong echo areas AH of the scanned image Sg and the standard image Ig.

Step 211: Determine whether the gel supplying unit supplies the gel on the ultrasound probe according to a result in Step 210. If yes, go to step 212; if no, go to step 213.

Step 212: The gel supplying unit coupled to the ultrasound probe supplies the gel on the ultrasound probe.

Step 213: End.

In addition, in step 204, the first threshold can be set to 0.2 mm. That is, when the distance difference between the positions of the pixels with the maximum signal intensity of the scanned image Sg and the standard image Ig is less than 0.2 mm, the thickness of the coated gel measures up to the standard. In step 208, the second threshold can be set to 15 percent. That is, when the intensity variation between the maximum signal intensity values corresponding to the scan lines in the strong echo areas AH of the scanned image Sg and the standard image Ig exceeds 15 percent, the connection of the coated gel measures up to the standard.

Furthermore, in step 211, a corresponding information that the consistency of the coated gel does not measure up can be displayed on the user surface, and a corresponding signal can be transmitted to the gel supplying unit so as to determine whether the gel supplying unit supplies the gel on the ultrasound probe, as detecting the coated gel coated on the ultrasound probe does not measure up. If the state of the coated gel coated on the ultrasound probe does not measure up, the gel supplying unit supplies the gel on the ultrasound probe. The present invention is not limited to an ultrasound scanner capable of automatically supplying the gel, and the gel can be supplied manually.

Accordingly, the ultrasound probe can be selectively on a contact scanning state or on a non-contact scanning state, and the ultrasound probe can generate the scanned image Sg and the standard image Ig under the non-contact scanning state for better accuracy.

Figure 5:
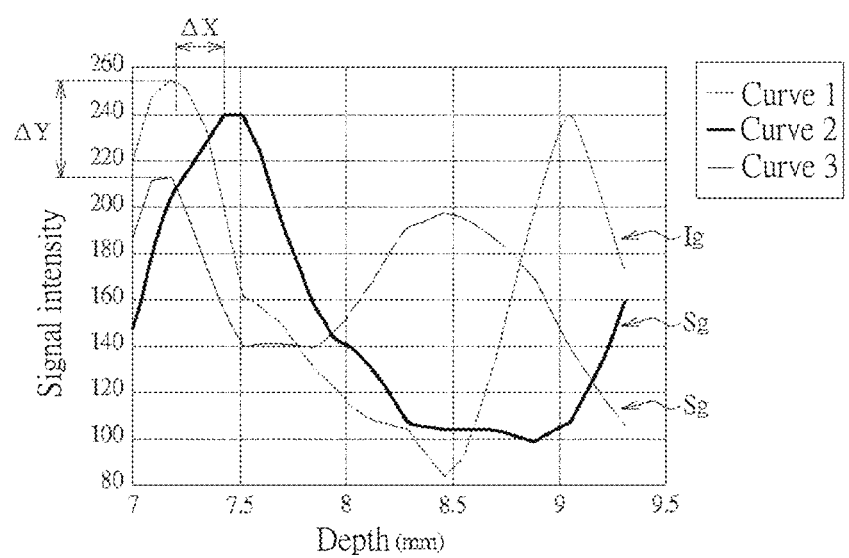
FIG. 5 is a diagram of signal intensity average values corresponding to different depths in the strong echo areas of a scanned image and the standard image in different conditions according to the embodiment of the present invention.

Please refer to FIG. 5. FIG. 5 is a diagram of signal intensity average values corresponding to different depths in the strong echo areas AH of the scanned image Sg and the standard image Ig in different conditions according to the embodiment of the present invention. The signal intensity average values corresponding to the different depths in the strong echo areas AH of the standard image Ig is illustrated as Curve 1. The signal intensity average values corresponding to the different depths in the strong echo areas AH of the scanned image Sg generated by the ultrasound probe coated with the coated gel under the non-contact scanning state is illustrated as Curve 2. The signal intensity average values corresponding to the different depths in the strong echo areas AH of the scanned image Sg generated by the ultrasound probe with the coated gel under the contact scanning state is illustrated as Curve 3.

In this embodiment, the distance difference $\Delta X$ between the positions of the pixels with the maximum signal intensity of Curve 1 and Curve 2 can be calculated. As the distance difference $\Delta X$ exceeds the first threshold, it can determine that the thickness of the coated gel does not measure up to the standard. For example, the first threshold can be 0.2 mm, and it can determine that the thickness of the coated gel does not measure up to the standard as the distance difference $\Delta X$ is greater than 0.2 mm. In addition, the intensity variation $\Delta Y$ between the maximum signal intensity values of Curve 1 and Curve 3 can be calculated. As the intensity variation $\Delta Y$ is lower than the second threshold, it can determine that the connection of the coated gel does not measure up to the standard. For Example, the second threshold can be 15 percent, and it can determine that the connection of the coated gel measure up to the standard as the intensity variation $\Delta Y$ exceeds 15 percent.

In contrast to the prior art, the method of the present invention includes detecting the state of the coated gel coated on the ultrasound probe for determining whether the thickness, the connection and the consistency of the coated gel coated on the ultrasound probe measure up. As the thickness, the connection and the consistency of the coated gel do not measure up, a corresponding information that the thickness, the connection and the consistency of the coated gel do not measure up can be displayed on the user interface, and the gel supplying unit can supply the gel on the ultrasound probe. Therefore, the performance of the ultrasound probe can be enhanced.

Those skilled in the art will readily observe that numerous modifications and alterations of the device and method may be made while retaining the teachings of the invention. Accordingly, the above disclosure should be construed as limited only by the metes and bounds of the appended claims.

What is claimed is:

1. A method of detecting a state of a coated gel coated on an ultrasound probe, the method comprising:
   coating a gel on the ultrasound probe;
   scanning and generating a scanned image;
   dividing the scanned image into a strong echo area and a weak echo area; and
   detecting signal variation in the strong echo area of the scanned image to determine the state of the coated gel coated on the ultrasound probe.

2. The method of claim 1, further comprising:
   generating a standard image by the ultrasound probe;
   calculating signal intensity average values corresponding to different depths according to a signal intensity distribution of scan lines of the standard image; and
   analyzing the signal intensity average values corresponding to the different depths statistically to generate a critical intensity value for dividing the standard image into a strong echo area and a weak echo area.

3. The method of claim 2, further comprising:
   calculating positions of pixels with maximum signal intensity corresponding to the scan lines in the strong echo areas of the scanned image and the standard image;
   calculating a distance difference between the positions of the pixels with the maximum signal intensity of the scanned image and the standard image; and
   determining whether the distance difference between the positions of the pixels with the maximum signal intensity of the scanned image and the standard image exceeds a first threshold.

4. The method of claim 3, further comprising:
   determining a thickness of the coated gel measures up as the distance difference between the positions of the pixels with the maximum signal intensity of the scanned image and the standard image is less than 0.2 mm, and determining the thickness of the coated gel does not measure up to display a corresponding information that the thickness of the coated gel does not measure up on a user interface as the distance difference between the positions of the pixels with the maximum signal intensity of the scanned image and the standard image exceeds the first threshold.

5. The method of claim 2, wherein the ultrasound probe is selectively on a contact scanning state or on a non-contact scanning state, and the ultrasound probe generates the scanned image and the standard image under the non-contact scanning state.

6. The method of claim 2, further comprising:
   calculating maximum signal intensity values corresponding to the scan lines in the strong echo areas of the scanned image and the standard image;
   calculating an intensity variation between the maximum signal intensity values corresponding to the scan lines in the strong echo areas of the scanned image and the standard image;
   determining whether the intensity variation between the maximum signal intensity values corresponding to the scan lines in the strong echo areas of the scanned image and the standard image is lower than a second threshold.

7. The method of claim 6, further comprising determining a connection of the coated gel measures up as the intensity variation between the maximum signal intensity values corresponding to the scan lines in the strong echo areas of the scanned image and the standard image exceeds 15 percent.

8. The method of claim 6, further comprising displaying a corresponding information that the connection of the coated gel does not measure up on a user interface, as the intensity variation between the maximum signal intensity values corresponding to the scan lines in the strong echo areas of the scanned image and the standard image is lower than the second threshold.

9. The method of claim 2, further comprising determining a consistency of the coated gel according to a distance difference between positions of pixels with maximum signal intensity of the scanned image and the standard image, and an intensity variation between maximum signal intensity values corresponding to the scan lines in the strong echo areas of the scanned image and the standard image.

10. The method of claim 1, further comprising a gel supplying unit coupled to the ultrasound probe supplying the gel on the ultrasound probe as determining the state of the coated gel does not measure up.

11. A method of supplying a gel on an ultrasound probe, the method comprising:
    providing a gel supplying unit coupled to the ultrasound probe;
    scanning and generating a scanned image;
    dividing the scanned image into a strong echo area and a weak echo area; and
    detecting signal variation in the strong echo area of the scanned image to selectively supply the gel on the ultrasound probe to form a coated gel by the gel supplying unit.

12. The method in claim 11, further comprising:
    generating a standard image by the ultrasound probe;
    calculating signal intensity average values corresponding to different depths according to a signal intensity distribution of scan lines of the standard image; and
    analyzing the signal intensity average values corresponding to the different depths statistically to generate a critical intensity value for dividing the standard image into a strong echo area and a weak echo area.

13. The method of claim 12, further comprising:
    calculating positions of pixels with maximum signal intensity corresponding to the scan lines in the strong echo areas of the scanned image and the standard image;
    calculating a distance difference between the positions of the pixels with the maximum signal intensity of the scanned image and the standard image; and
    determining whether the distance difference between the positions of the pixels with the maximum signal intensity of the scanned image and the standard image exceeds a first threshold.

14. The method of claim 13, further comprising:
determining a thickness of the a coated gel coated on an ultrasound probe measures up as the distance difference between the positions of the pixels with the maximum signal intensity of the scanned image and the standard image is less than 0.2 mm, and determining the thickness of the coated gel does not measure up to display a corresponding information that the thickness of the coated gel does not measure up on a user interface as the distance difference between the positions of the pixels with the maximum signal intensity of the scanned image and the standard image exceeds the first threshold.

15. The method of claim 12, wherein the ultrasound probe is selectively on a contact scanning state or on a non-contact scanning state, and the ultrasound probe generates the scanned image and the standard image under the non-contact scanning state.

16. The method of claim 12, further comprising:
calculating maximum signal intensity values corresponding to the scan lines in the strong echo areas of the scanned image and the standard image;
calculating an intensity variation between the maximum signal intensity values corresponding to the scan lines in the strong echo areas of the scanned image and the standard image; and
determining whether the intensity variation between the maximum signal intensity values corresponding to the scan lines in the strong echo areas of the scanned image and the standard image is lower than a second threshold.

17. The method of claim 16, further comprising determining a connection of the coated gel measures up as the intensity variation between the maximum signal intensity values corresponding to the scan lines in the strong echo areas of the scanned image and the standard image exceeds 15 percent.

18. The method of claim 16, further comprising displaying a corresponding information that the connection of the coated gel does not measure up on a user interface, as the intensity variation between the maximum signal intensity values corresponding to the scan lines in the strong echo areas of the scanned image and the standard image is lower than the second threshold.

19. The method of claim 12, further comprising determining a consistency of the coated gel according to a distance difference between positions of pixels with maximum signal intensity of the scanned image and the standard image, and an intensity variation between maximum signal intensity values corresponding to the scan lines in the strong echo areas of the scanned image and the standard image.

20. The method of claim 11, further comprising the gel supplying unit coupled to the ultrasound probe supplying the gel on the ultrasound probe as determining a state of the coated gel coated on the ultrasound probe does not measure up.

* * * * *